United States Patent
Syms (10) Patent No.: US 7,189,966 B2
(45) Date of Patent: Mar. 13, 2007

(54) APPARATUS FOR ION DESOLVATION IN FAIMS

(75) Inventor: Jerry Syms, Orleans (CA)

(73) Assignee: National Research Council of Canada, Ottawa (CA)

( * ) Notice: Subject to any disclaimer, the term of this patent is extended or adjusted under 35 U.S.C. 154(b) by 73 days.

(21) Appl. No.: 11/133,183

(22) Filed: May 20, 2005

(65) Prior Publication Data

US 2005/0258363 A1   Nov. 24, 2005

(30) Foreign Application Priority Data

May 21, 2004   (CA) .................................... 2468586

(51) Int. Cl.
*H01J 49/40*   (2006.01)
(52) U.S. Cl. ...................... 250/292; 250/291; 250/290; 250/282; 250/283; 250/287
(58) Field of Classification Search ..................... None
See application file for complete search history.

(56) References Cited

U.S. PATENT DOCUMENTS 7,005,633 B2 *   2/2006   Guevremont et al.   ........ 250/287

* cited by examiner

*Primary Examiner*—Nikita Wells
*Assistant Examiner*—Zia R. Hashmi
(74) *Attorney, Agent, or Firm*—Freedman & Associates (57) ABSTRACT

Ion separation in a FAIMS analyzer is affected by the presence of neutral species and solvent vapor. A diffuser element, which is fabricated from a porous material, is disposed within a curtain gas chamber adjacent to the FAIMS ion inlet, such that a flow of a curtain gas is blocked from flowing directly out through a curtain gas orifice. The porous material creates a pressure drop across the diffuser and results in the flow of curtain gas being provided out of the curtain gas orifice, along a direction that is approximately perpendicular to a plane containing the curtain gas orifice. The perpendicular gas flow opposes ions traveling toward the curtain gas orifice from an ionization source, thereby desolvating the ions. Providing a perpendicular curtain gas flow for desolvating ions reduces the ion losses that are normally associated with the curtain gas flow deflecting some of the ions away from the curtain gas orifice and toward a curtain plate electrode.

26 Claims, 8 Drawing Sheets

APPARATUS FOR ION DESOLVATION IN FAIMS

FIELD OF THE INVENTION

The instant invention relates generally to High Field Asymmetric Waveform Ion Mobility Spectrometry (FAIMS). In particular, the instant invention relates to a method and apparatus for providing a flow of desolvated ions into FAIMS.

BACKGROUND

A wide variety of ionization sources, including atmospheric pressure ionization sources such as electrospray ionization or ESI, have been described for use with FAIMS. Unfortunately, ion separation in FAIMS is highly susceptible to contamination by neutral species and/or solvent vapor and liquid droplets. Accordingly, it is desirable to desolvate ions of an analyte species prior to introducing the ions into FAIMS, and to avoid introduction of neutral species into the FAIMS analyzer.

Typically, ions are produced at the ionization source and an electric field is established so as to direct the ions toward an ion inlet orifice into an analyzer region of FAIMS. Neutral species and droplets of the liquid solvent are prevented from entering the analyzer region by providing an outwardly directed flow of a desolvation gas. For instance, when a carrier gas is provided for transporting ions through the FAIMS analyzer region, often a portion of the carrier gas is made to pass outwardly through the ion inlet and perform the role of the desolvation gas. Alternatively, a separate curtain plate region is provided between the ionization source and the ion inlet into FAIMS. During use, a flow of a curtain gas provided into the curtain plate region splits into two separate flows; a first flow that is directed outward through an opening in the curtain plate and toward the ionization source, and a second flow through the ion inlet into the FAIMS analyzer region. Advantageously, the first flow desolvates the ions whilst the second flow assists in transporting the desolvated ions into the FAIMS analyzer region.

Of course, ions experience a variety of forces within the region between the ionization source and the FAIMS analyzer region. On the one hand, the force associated with the electric field pushes the ions in a direction generally toward the FAIMS analyzer region, whilst on the other hand the force associated with the outward flow of the desolvation gas pushes the ions in a direction generally away from the FAIMS analyzer region. In order to obtain high ion transmission efficiency into the FAIMS analyzer region, it is essential that these two opposing forces be well defined, and that the forces cooperate one with the other to direct the ions through the opening in the curtain plate or through the ion inlet directly into the FAIMS analyzer region.

Unfortunately, the flow of gas outward through either the opening in the curtain plate or the ion inlet tends not to be very close to perpendicular to the respective opening. In fact, the outward flow of gas has been found to be biased toward a side of the opening that is along the direction of gas flow within the region on the opposite side of the opening. This is because the gas has momentum, and tends to continue moving in the same direction as it passes outwardly through the openings. Accordingly, the flow of gas that is intended to desolvate the ions and prevent entry of neutral species also tends to deflect the ions away from the opening. If the deflection is of sufficient magnitude so as to cause some of the ions to impinge upon a surface of an electrode through which the opening is defined, then the efficiency of ion transmission into the FAIMS analyzer is reduced.

It would be advantageous to provide a system and method for introducing ions into a FAIMS analyzer that overcomes at least some of the above-mentioned limitations of the prior art.

SUMMARY OF THE INVENTION

According to an aspect of the instant invention, provided is an apparatus for separating ions, comprising: a first electrode having a first orifice defined therethrough; a FAIMS analyzer comprising a second electrode having a second orifice defined therethrough, the second orifice spaced-apart from and approximately aligned with the first orifice when the apparatus is in an assembled condition; a curtain gas chamber defined by a space between the first electrode and the second electrode and being dimensioned larger than a size of either one of the first orifice and the second orifice, the curtain gas chamber including a third orifice for providing a flow of a gas from a gas source into the curtain gas chamber; and, a diffuser comprising a porous material and having a length, the diffuser including a passageway extending along the length between a first end of the diffuser and an opposite second end of the diffuser, the passageway being open at the first end and at the second end, the diffuser being disposed within the curtain gas chamber between the third orifice and each of the first and second orifices, and such that both of the first orifice and the second orifice are aligned with the passageway through the diffuser.

According to an aspect of the instant invention, provided is an apparatus for separating ions, comprising: a FAIMS analyzer comprising a first electrode and a second electrode disposed in a spaced-apart relationship one relative to the other so as to define an analyzer region therebetween, the first electrode having an inlet orifice defined therethrough for providing fluid communication between the analyzer region and a region that is external to the analyzer region; a curtain gas chamber disposed within the region that is external to the analyzer region and in fluid communication with the analyzer region via the inlet orifice, the curtain gas chamber including a curtain gas inlet for receiving a flow of a curtain gas from a curtain gas source, and including a curtain plate electrode having an outlet orifice defined therethrough; and, a diffuser disposed within the curtain gas chamber between the first electrode and the curtain plate electrode, the diffuser comprising a porous material having a passageway defined therethrough and open at both ends such that the inlet orifice and the outlet orifice are in fluid communication one with the other via the passageway, and such that the curtain gas inlet is in fluid communication with each of the inlet orifice and the outlet orifice via a plurality of gas flow-paths defined through the porous material.

According to an aspect of the instant invention, provided is an apparatus for separating ions, comprising: a FAIMS analyzer comprising a first electrode and a second electrode disposed in a spaced-apart relationship one relative to the other so as to define an analyzer region therebetween, the first electrode having an inlet orifice defined therethrough for providing fluid communication between the analyzer region and a region that is external to the analyzer region; a curtain gas chamber disposed adjacent to the inlet orifice, the curtain gas chamber including a curtain gas inlet for receiving a flow of a curtain gas from a curtain gas source and a curtain gas outlet for providing a flow of the curtain gas; and, means for restricting gas flow between the curtain gas inlet and the curtain gas outlet such that the flow of curtain gas out of the curtain gas outlet is provided along a direction substantially perpendicular to a plane containing the curtain gas outlet.

According to an aspect of the instant invention, provided is a method of separating ions, comprising: providing a FAIMS analyzer region that is in fluid communication with a curtain gas region via a first orifice; providing an ionization source that is in fluid communication with the curtain gas region via a second orifice; providing a flow of a curtain gas into the curtain gas region via a third orifice that is spaced-apart from each of the first orifice and the second orifice; directing the flow of a curtain gas through a porous wall of a diffuser element that is disposed within the curtain gas region and into a passageway within the interior of the diffuser element so as to restrict the flow of a curtain gas between the third orifice and each one of the first orifice and the second orifice; providing a flow of the curtain gas along the passageway and out through the second orifice along a direction that is substantially perpendicular to a plane containing the second orifice; and, directing a flow of ions from the ionization source toward the second orifice so as to desolvate the ions in the flow of the curtain gas.

BRIEF DESCRIPTION OF THE DRAWINGS

Exemplary embodiments of the invention will now be described in conjunction with the following drawings, in which similar reference numerals designate similar items.

DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
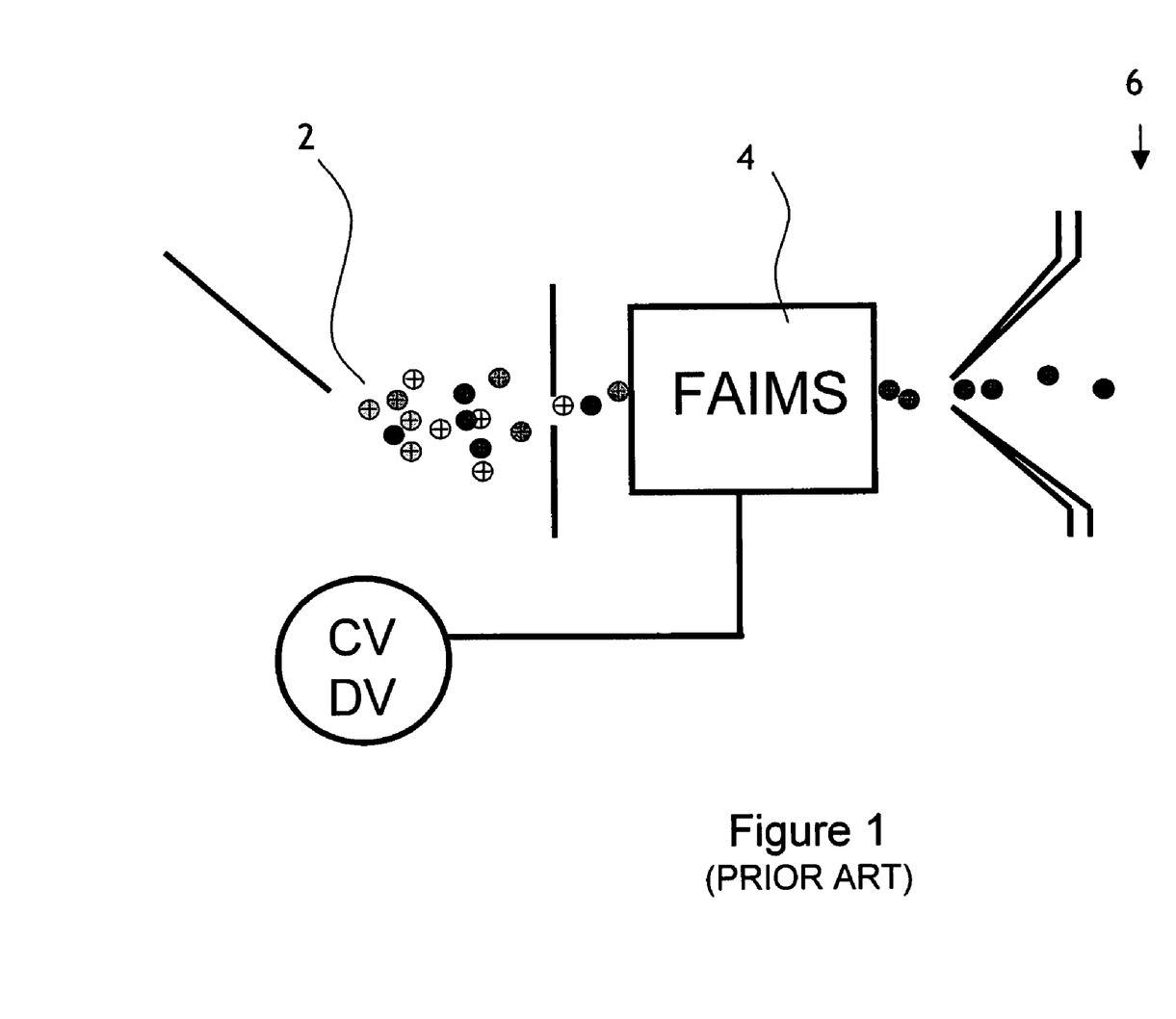
FIG. 1 is a simplified block diagram showing a tandem arrangement including an ion source, a FAIMS, and a mass spectrometer.

FIG. 1 is a simplified block diagram showing a tandem arrangement including an ion source 2, a FAIMS 4, and a mass spectrometer 6. In the specific and non-limiting example of FIG. 1, an electrospray ionizer is shown. However, many other suitable ion sources are known, including photoionization sources, atmospheric pressure MALDI, radioactivity based sources, corona discharge sources, and other rf-based discharge sources, to name just a few non-limiting examples.

Figure 2:
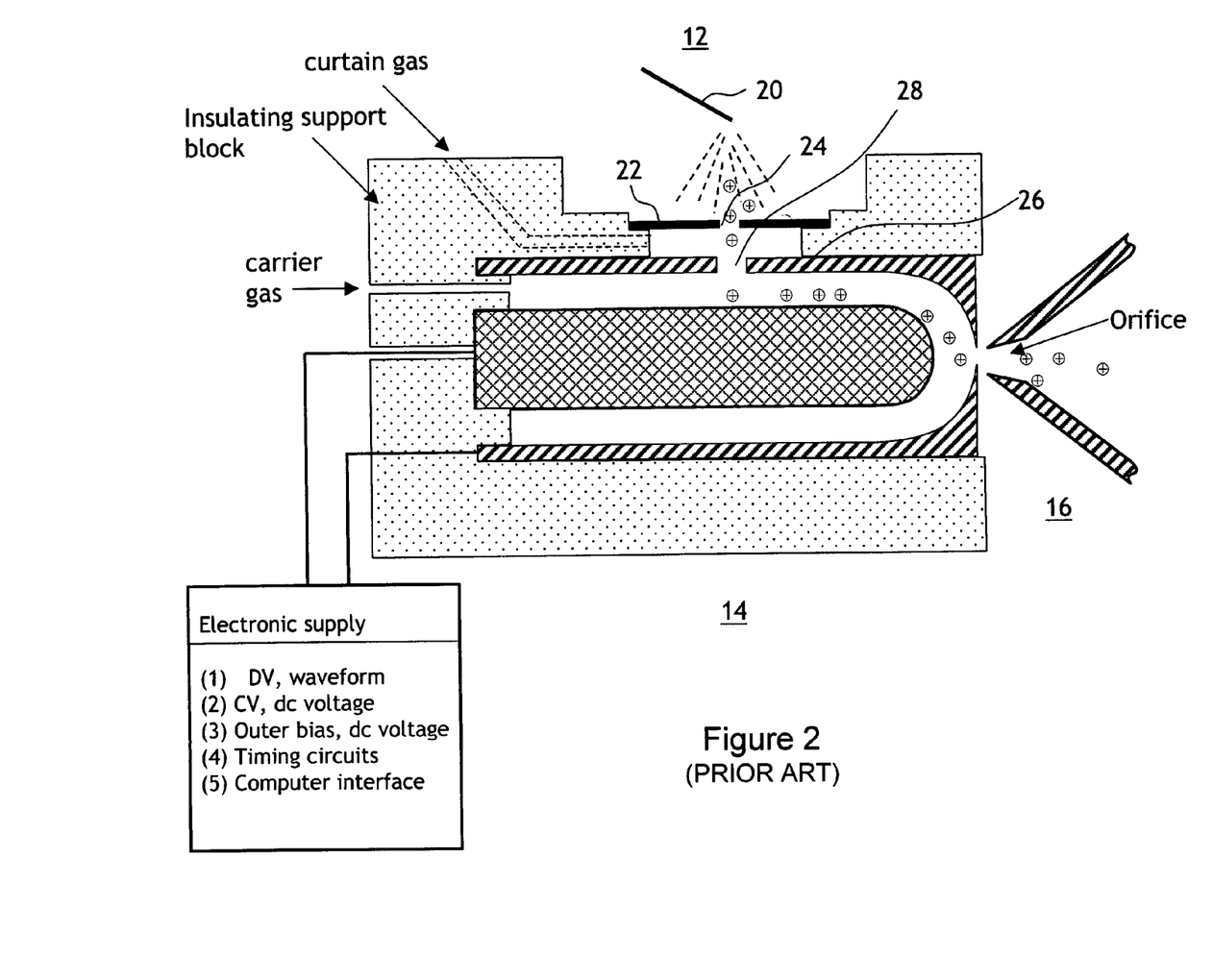
FIG. 2 is a longitudinal cross-sectional view of a prior art system including an electrospray ion source disposed in fluid communication with an ion inlet of a FAIMS, the FAIMS being mounted in and supported by an insulating material.

FIG. 2 is a simplified block diagram showing a tandem arrangement according to the prior art, including an ion source 12, a FAIMS 14, and a mass spectrometer 16. The ion source 12 includes an electrospray needle 20 through which a liquid sample flows. The electrospray needle 20 is held at high voltage relative to a curtain plate 22 so that the liquid is caused to break into a very fine spray as the liquid issues from the tip of the electrospray needle 20, the sample components within the droplets of the spray are ionized, and the ions are driven by the electric field towards the curtain plate 22. Some of the ions travel through the opening 24 in the curtain plate 22. An electric field between the curtain plate and the outer electrode 26 of FAIMS further drives the ions towards the ion inlet 28 of FAIMS.

Typically, the ionization source 12 shown at FIG. 2 includes provision for affecting the temperature, such as by heating, of either the ionization process or a not illustrated chamber surrounding the source 12. For example, the most common type of heat addition is through the application of a nebulizer gas in concentric arrangement around the electrospray needle, where the nebulizer gas is pre-heated to promote desolvation of the small droplets formed by electrospray ionization. Alternatively, a stream of hot gas may be directed toward the plume of ions/droplets leaving the electrospray needle 20. Optionally, the not illustrated chamber that houses the ionization source 12 is operated at elevated temperature.

Figure 3:
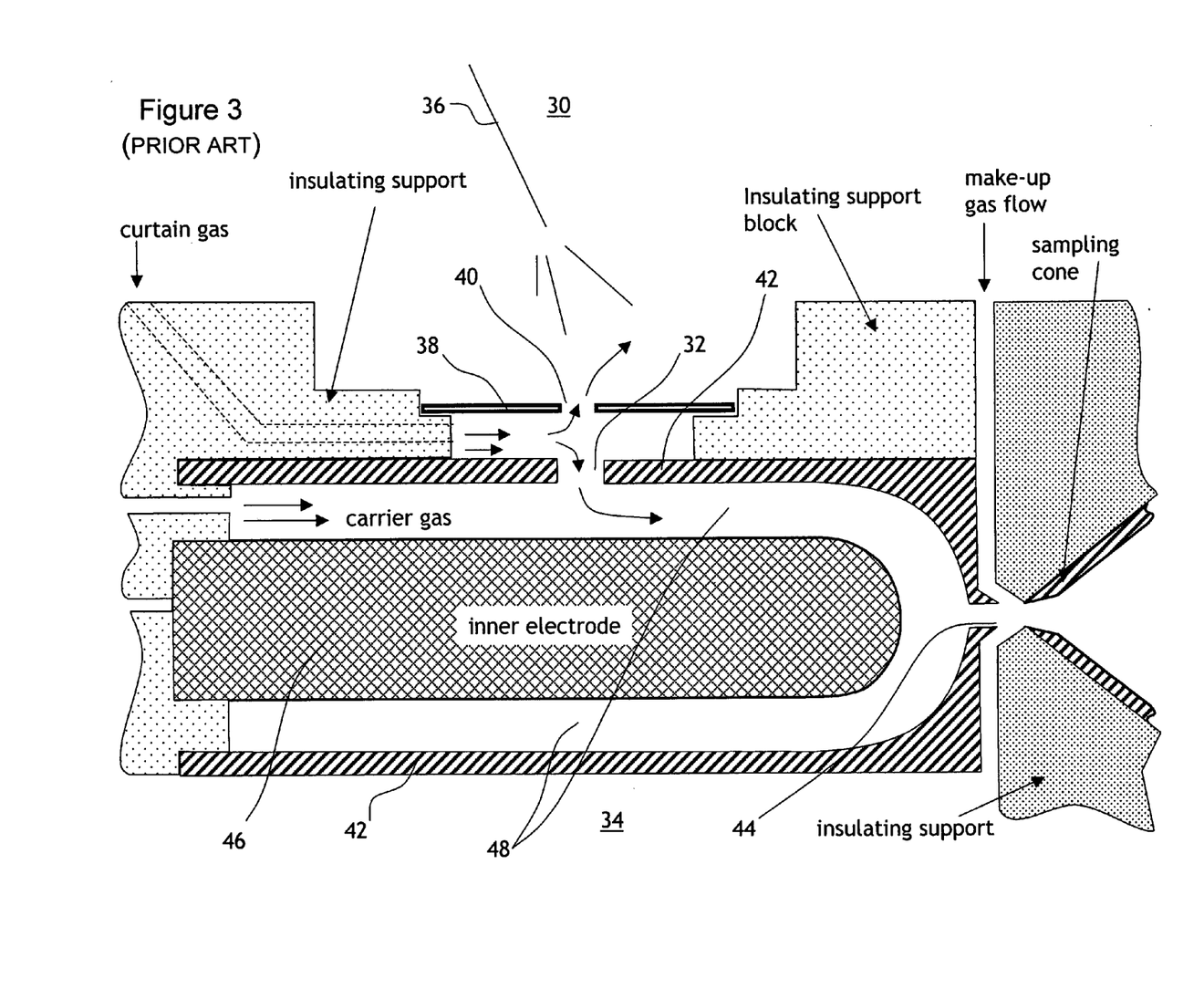
FIG. 3 is an expanded view of FIG. 2 illustrating the flows of curtain gas in a prior art system.

Referring now to FIG. 3, shown is a longitudinal cross-sectional view of an electrospray ion source 30 disposed in fluid communication with an ion inlet 32 of a FAIMS 34, according to the prior art. In FIG. 3, the ions are formed near the tip of an electrospray needle 36 and drift towards a curtain plate 38. A curtain gas, introduced below the curtain plate, divides into two flows, one of which exits through an aperture 40 in the curtain plate 38, to prevent neutrals and droplets from entering the curtain plate aperture 40. Ions are driven against this gas by a voltage gradient between the needle 36 and the curtain plate 38. A field generated between the curtain plate 38 and a FAIMS outer electrode 42 further drives ions that pass through the aperture 40 in the curtain plate 38 towards the ion inlet 32 of FAIMS 34. A portion of the curtain gas flows into the ion inlet 32 and carries the ions along the length of the FAIMS electrodes to an ion outlet 44, and into a not illustrated mass spectrometer.

A high voltage asymmetric waveform is applied to an inner electrode 46 of FAIMS 34, to produce an electric field that causes ions within an annular space between the inner electrode 46 and the outer electrode 42, which annular space is referred to as the analyzer region 48, to oscillate between the inner electrode 46 and the outer electrode 42. The waveform is generated in such a way to cause the ions to move in a first direction in a strong field for a short time, followed by motion in the other direction in a weaker field for a longer time. Absent any change in ion mobility between the high field and low field portions of this applied asymmetric waveform, the ion is expected to return to its original position relative to the surface of the electrodes after each cycle of the waveform if the effects of diffusion or ion-ion repulsion are not considered. In practice however, the mobility of many ions is different in strong and weak electric fields and for these ions the position after one cycle of the waveform is not identical to its starting position relative to the electrode surfaces. A second, direct current voltage, which is referred to as the compensation voltage (CV), is applied to eliminate or compensate for this change of position. If the compensation voltage is of a magnitude that eliminates or compensates for the change of position that a particular ion species would exhibit under the influence of one cycle of the high voltage asymmetric waveform would occur absent the compensation voltage, the ion returns to the same relative location after each cycle of the waveform. Thus the ion does not migrate towards one or the other of the electrodes and is transmitted through FAIMS 34. Other ions, for which the compensation voltage is too high or too low to compensate for the net displacement of the ion relative to the electrodes during one cycle of the waveform, drift toward an electrode and are unable to pass through FAIMS 34.

Figure 4:
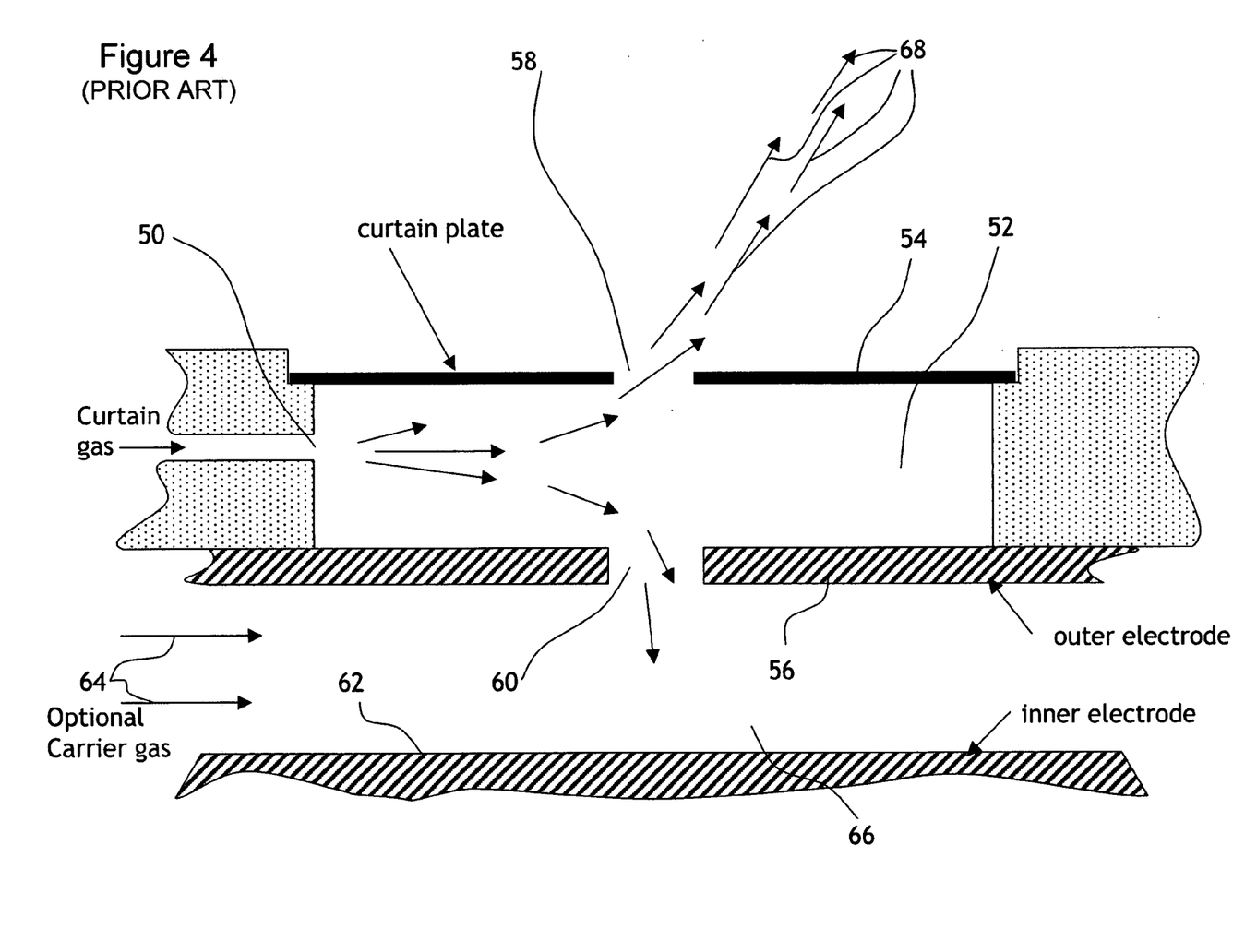
FIG. 4 is an expanded view of a prior art curtain plate region used for desolvation of ions prior to their entry into the FAIMS analyzer region.

Referring now to FIG. 4, shown is a cross sectional view of the curtain plate region of a prior art system. The curtain gas is provided through a curtain gas inlet 50 and enters the curtain chamber 52 located between the curtain plate 54 and the outer electrode 56 of FAIMS. A portion of the curtain gas flows outward through the opening 58 in the curtain plate 54 and a second portion flows into the ion inlet 60 of FAIMS. The relative volumes of these two flows are controlled by the flow of gas out of the ion outlet of FAIMS and the flow of carrier gas 64, if any, that is added to the analyzer region 66 between the outer electrode 56 and the inner electrode 62 of FAIMS. The flow of gas out of opening 58 of the curtain plate 54 assists in the desolvation of the ions that are produced by the not illustrated ionization source.

In FIG. 4, the one portion of the gas flowing into the curtain chamber 52 flows by the most direct, or shortest, route between the curtain gas inlet 50 and the opening 58 in the curtain plate 54. Similarly the second portion of the curtain gas follows the most direct, i.e. the shortest route between the curtain gas inlet 50 and the ion inlet 60 of FAIMS.

It is a disadvantage of the desolvation system shown in FIG. 4 that the curtain gas flows in very directed streams towards the exits of the curtain chamber, causing the gas flowing out of the opening 58 in the curtain plate 54 to form a narrowly directed stream. It is a disadvantage that this stream does not travel in a perpendicular direction relative to the curtain plate, but rather flows at an angle out of the opening 58 in the curtain plate 54. This angled, narrow beam is shown schematically by the gas flow arrows 68 in FIG. 4. This angled, narrow flow has been shown to exist by computational fluid dynamics (CFD) calculations.

Figure 5:
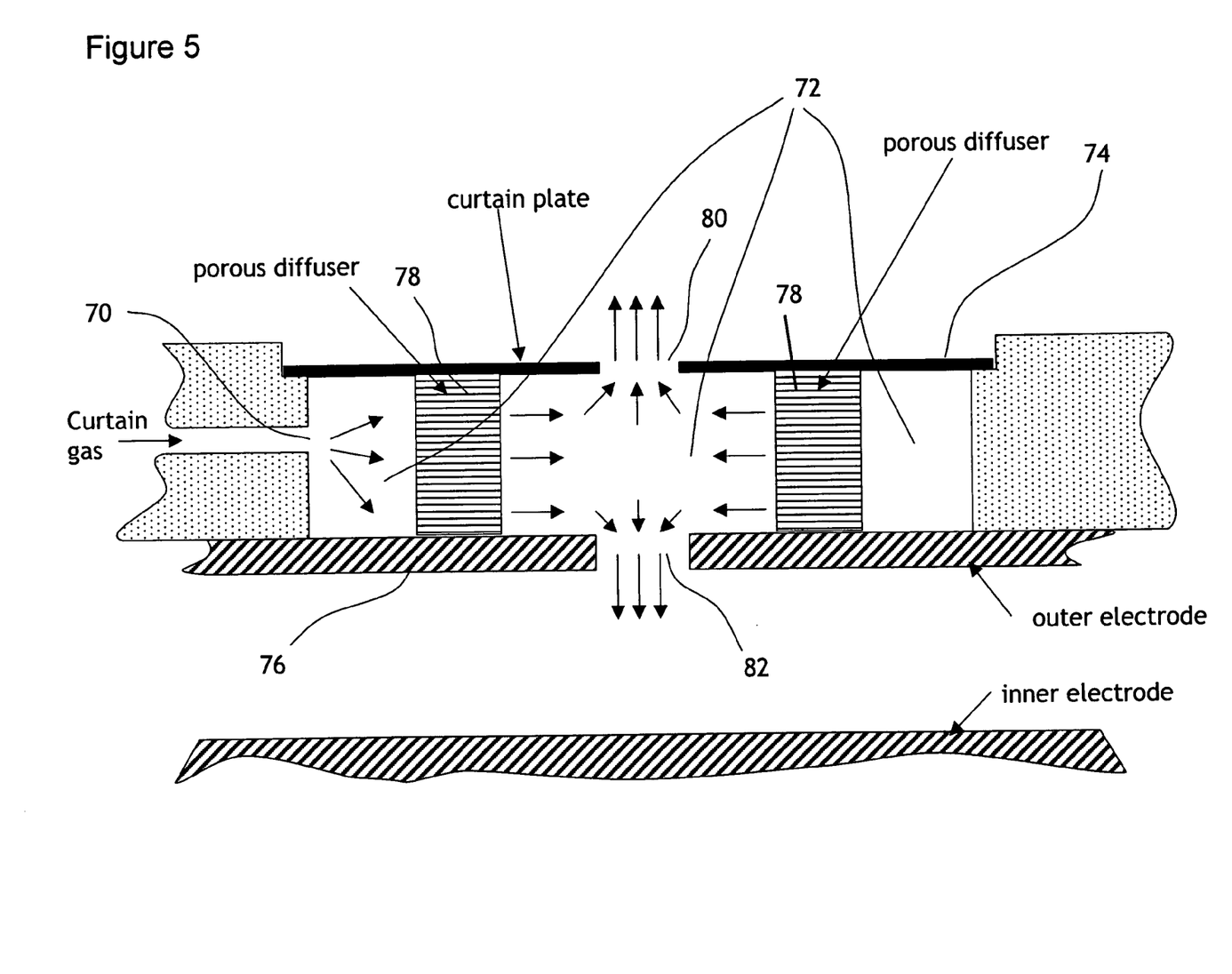
FIG. 5 is an expanded view of the curtain plate region, with a porous diffuser ring according to an embodiment of the instant invention.

Referring now to FIG. 5, shown is a cross sectional view of a curtain plate region of a system according to an embodiment of the instant invention, for modifying the narrow and directed gas flows that were discussed with reference to FIG. 4. In FIG. 5 a curtain gas flow is provided through gas inlet 70 to the curtain chamber 72 located between a curtain plate 74 and the outer electrode 76 of FAIMS. However, a cylinder of a porous material, called diffuser 78, is positioned to entirely surround the opening 80 of the curtain plate 74 and the ion inlet 82 of FAIMS. The diffuser 78 is positioned to fit entirely in the vertical space between the curtain plate 74 and the outer electrode 76, so that the curtain gas provided through gas inlet 70 has to pass through a portion of the diffuser 78 in order to reach the opening 80 of the curtain plate 74 or the ion inlet 82 of FAIMS via a central passageway of the diffuser 78. Optionally, the diffuser 78 makes a substantially gas-tight seal with the curtain plate 74 about the opening 80 and makes a substantially gas-tight seal with the outer electrode 76 about the ion inlet 82. The opening 80 and the ion inlet 82 are in fluid communication via the central passageway of the diffuser.

Referring again to FIG. 5, the diffuser 78 blocks the shortest pathway, more specifically a shortest gas flow-path, between the gas inlet 70 to either the opening 80 or the ion inlet 82 and creates a restriction to the gas which results in a slight increase in pressure within the curtain chamber 72, in the region outside the cylindrical diffuser, when compared to the region of the chamber 72 that is surrounded by the diffuser and includes the opening 80 and the ion inlet 82. The diffuser causes the gas flow entering the curtain chamber 72 via the gas inlet 70 to distribute into a plurality of gas flows passing through the diffuser 78 and thus acts to modify the gas flows exiting via the opening 80 of the curtain plate 74 and the ion inlet 82 of FAIMS. Accordingly, the porous material of the diffuser 78 is optionally selected from any material that is suitable for effecting such a restriction to gas flow, as a result of gas flowing through a plurality of gas flow-paths defined therethrough, so as to create the pressure drop across the diffuser. Some non-limiting examples of suitable porous materials include an organic or inorganic sponge-like material having tortuous channels defined therethrough, an organic or inorganic material having approximately straight passageways defined therethrough, or a sheet material having a plurality of openings defined therethrough, such as for example perforations. Furthermore, the cross-sectional areas of the individual openings or passageways of the porous material optionally are large or small compared to the length of the individual openings or passageways. The key is that the material presents a restriction to gas flow such that there is pressure drop from the curtain gas inlet side to the region that is in communication with the curtain plate opening and the ion inlet.

The above-mentioned increase in pressure has two beneficial effects. First, the diffuser 78 prevents the curtain gas from flowing along a shortest path between the inlet 70 and either possible curtain gas outlet. Secondly, the pressure differential results in flow through all parts of the diffuser 78, including the portion of the diffuser 78 that is located remotely from the gas inlet 70. As shown in FIG. 5 the gas flowing approximately uniformly through all portions of the diffuser 78 results in a gas flow out of the opening 80 of the curtain plate 74 that is approximately vertical in the figure, that is to say perpendicular relative to the curtain plate 74. Similarly the flow through the ion inlet 82 is flowing approximately perpendicularly relative to the outer electrode 76 of FAIMS.

Referring again to FIG. 5, it is an unforeseen advantage of the diffuser 78, that the flow out of opening 80 of the curtain plate 74 has lower velocity than absent the diffuser 78. Since the flow out of the opening 80 is approximately vertical, the entire cross section of the opening is available and the outwards flow is approximately uniform. At a fixed volume of gas, this maximized flow cross-section yields the minimum possible gas flow velocity. Referring back to FIG. 4, assuming that the same fixed volume of the gas flows out of the opening 58 in the curtain plate 54 at an angle relative to the curtain plate 54, the velocity of the flow is higher than that of FIG. 5, since the cross section of the opening 58 appears to be smaller due to the fact that the gas travels through the opening 58 at an angle other than normal to it. As a non-limiting example if the flow out of the opening is traveling approximately at 45 degrees relative to the curtain plate 54, the opening that is actually 0.01 cm² appears to be about (0.01)cosine(45°) or about 70% of its actual area. If the gas flow volume remains unchanged, the velocity is about 40% higher than if the gas flowed out of the opening in a direction approximately normal to the curtain plate 54.

It is a disadvantage of the higher velocity of gas in the system shown in FIG. 4 relative to the flow shown in FIG. 5, that some of the ions produced at the not shown ion source are driven away or deflected from the opening 58 in the curtain plate 54, and the efficiency of ion transmission through opening 58 is decreased.

Referring again to FIG. 5 it is therefore an advantage of the diffuser 78 that the gas flows in a uniform manner out of the opening 80 of the curtain plate 74, and that the outward flow velocity is minimized and the flow is distributed over a maximum region normal to the opening 80. The ions that are arriving at the opening 80 of the curtain plate 74 pass through a region of curtain gas that assists in desolvating the ions. Referring again to FIG. 4, some ions may arrive near the opening 58 without encountering the curtain gas flow, which in FIG. 4 flows out of the opening 58 at an angle other than normal to the curtain plate 54. Referring again to FIG. 5 it is beneficial to the desolvation process that the ions move against the flow of curtain gas for as long as possible. The curtain gas serves to carry the solvent away from the ion and to provide heat energy to the desolvating droplet as the desolvation process proceeds. Ideally the curtain gas flows in a broad stream along a line from the opening 80 of the curtain plate 74 towards the ionizer source. It is beneficial to maximize the region between the ionizer source and the opening 80 of the curtain plate 74 where the ion passes through the curtain gas.

Figure 6:
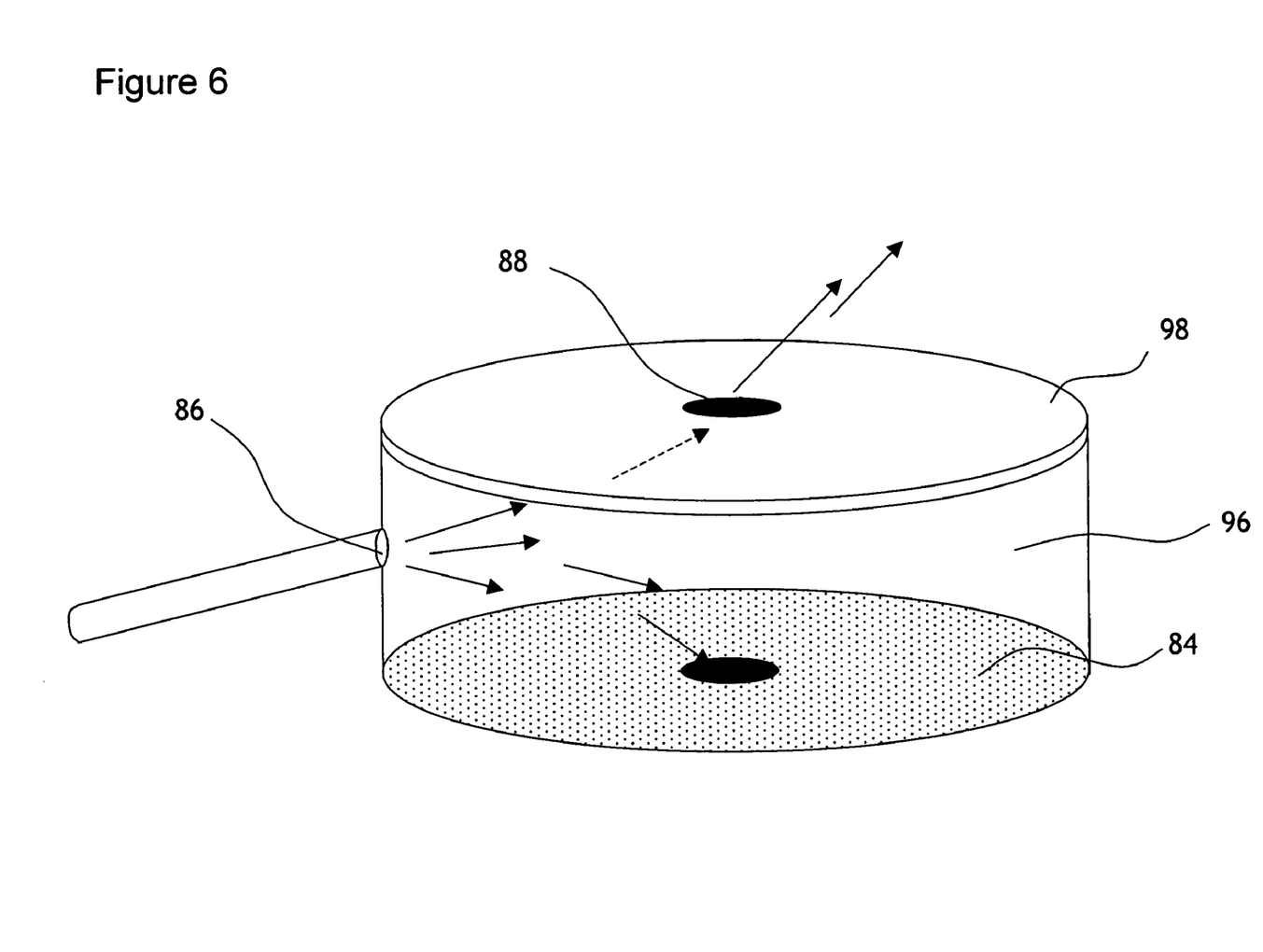
FIG. 6 is a simplified 3-dimensional schematic diagram showing the flow of curtain gas entering the space between the curtain plate and the outer electrode of a prior art FAIMS.

FIG. 6 illustrates, in 3-dimensional schematic view the curtain gas chamber 96 located between curtain plate 98 and the outer electrode 84 of FAIMS absent a diffuser. As discussed with reference to FIG. 4, the curtain gas delivered from gas inlet 86 flows in an approximately direct pathway between the inlet 86 and the opening 88 in the curtain plate 98. The gas, having momentum, continues along this path and exits from the opening 88 in the curtain plate 98 at an angle other than normal to the curtain plate 98.

Figure 7:
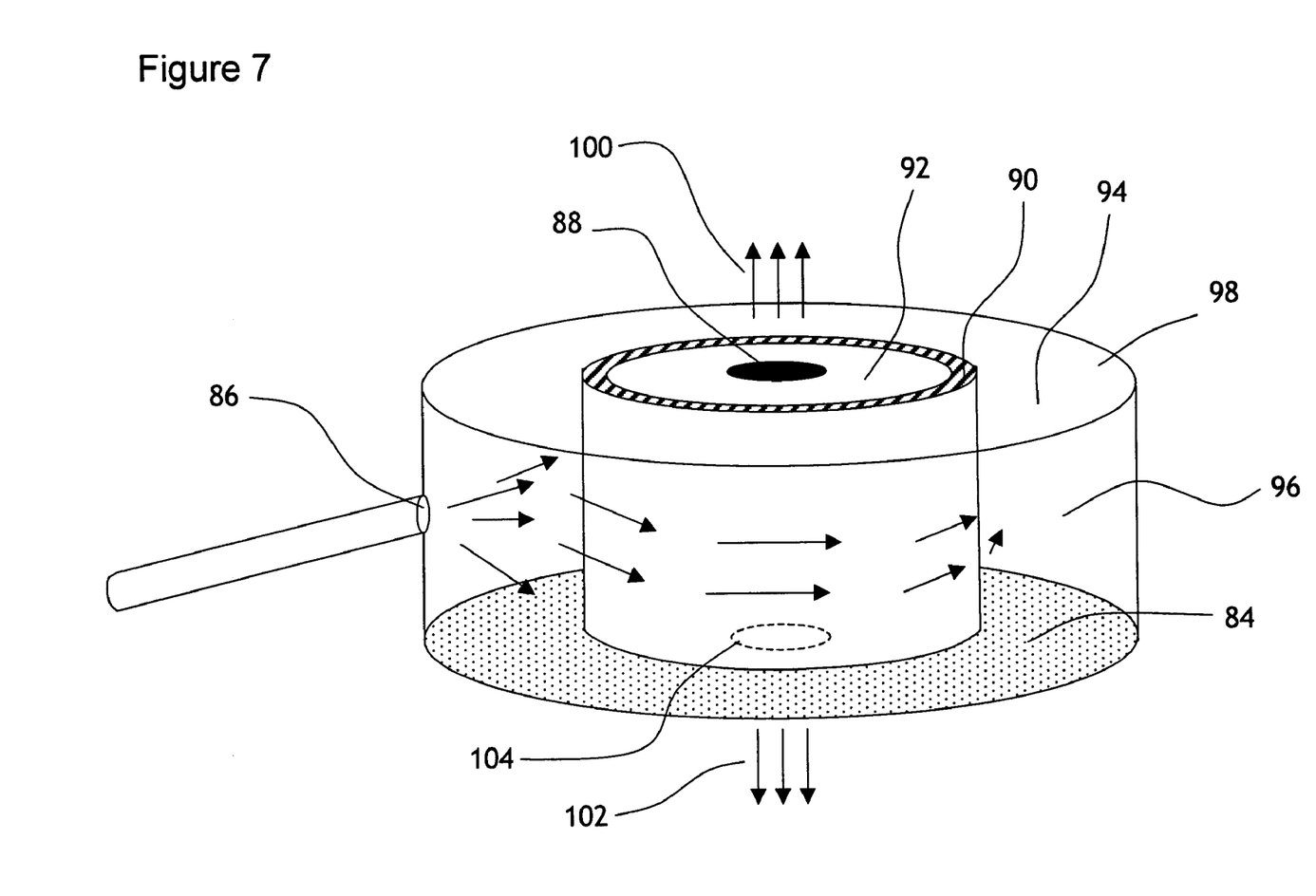
FIG. 7 illustrates the flow of curtain gas through the space between the curtain plate and outer electrode of a FAIMS including an insert of a cylinder of porous material acting as a diffuser according to an embodiment of the instant invention; and, FIG. 8 illustrates a simplified flow diagram of a method according to an embodiment of the instant invention.

FIG. 7 illustrates in 3-dimensional schematic view the cylindrical porous diffuser 90 located between curtain plate 98 and the outer electrode 84 of FAIMS. As discussed with reference to FIG. 5, the curtain gas delivered from gas inlet 86, which would be expected to flow in an approximately direct pathway between the inlet 86 and the opening 88 in the curtain plate 98, is intercepted by the diffuser 90. The diffuser 90 creates a pressure differential between an inside region, for instance passageway 92, and an outside region 94. The gas fills the outside region 94 and flows through the diffuser 90 approximately uniformly everywhere around its circumference. Since the gas flows into the inside region, for instance passageway 92, of the curtain gas chamber 96 from all directions this results in a gas flow 100 out of the opening 88 in the curtain plate 92 which is approximately perpendicular to the curtain plate 98. Once beyond the edges of a not illustrated insulating material, which supports the curtain plate 98 in a spaced-apart arrangement with the outer electrode 84 of FAIMS, the gas flow 100 begins to disperse, with some directional changes. Similarly, the portion 102 of curtain gas exiting the curtain gas chamber 96 through an ion inlet 104 into a not illustrated FAIMS analyzer region is flowing approximately normal to the surface of the outer electrode 84 of FAIMS.

Figure 8:
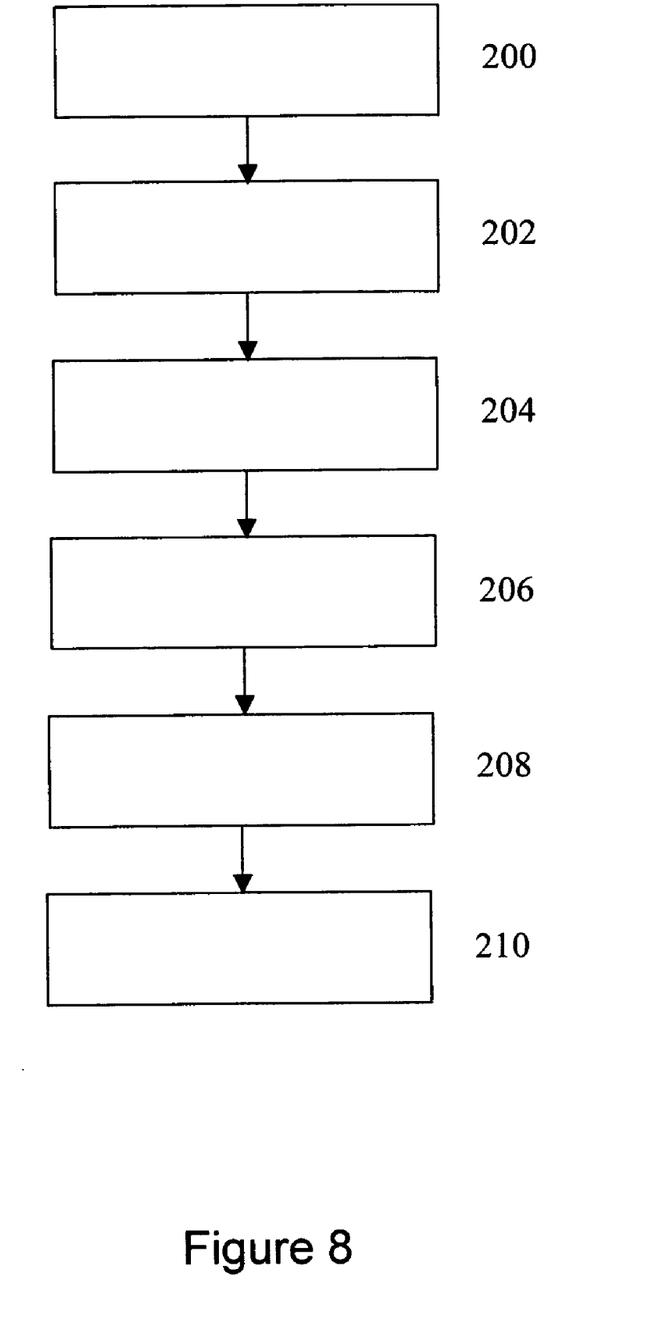

Referring now to FIG. 8, shown is a simplified flow diagram of a method according to an embodiment of the instant invention. At step 200 a FAIMS analyzer region is provided that is in fluid communication with a curtain gas region via a first orifice. At step 202 an ionization source is provided that is in fluid communication with the curtain gas region via a second orifice. At step 204 a flow of a curtain gas is provided into the curtain gas region via a third orifice that is spaced-apart from each of the first orifice and the second orifice. At step 206 the flow of a curtain gas is directed through a porous wall of a diffuser element that is disposed within the curtain gas region and into a passageway within the interior of the diffuser element so as to restrict the flow of a curtain gas between the third orifice and each one of the first orifice and the second orifice. At step 208 a flow of the curtain gas is provided along the passageway and out through the second orifice along a direction that is substantially perpendicular to a plane containing the second orifice. At step 210 a flow of ions from the ionization source is directed toward the second orifice so as to desolvate the ions in the flow of the curtain gas that has passed through the second orifice.

As described above, means for restricting gas flow is provided within the curtain chamber adjacent to an ion inlet orifice of FAIMS. Such means for restricting gas flow includes the diffuser 78, 90 illustrated in FIGS. 5 and 7, respectively. The means for restricting gas flow includes a porous material. As was described above, the porous material of the diffuser 78, 90, is optionally selected from any material that is suitable for effecting such a restriction to gas flow, as a result of gas flowing through a plurality of gas flow-paths defined therethrough, so as to create the pressure drop across the diffuser. Some non-limiting examples of suitable porous materials include an organic or inorganic sponge-like material having tortuous channels defined therethrough, an organic or inorganic material having approximately straight passageways defined therethrough, or a sheet material having a plurality of openings defined therethrough, such as for example perforations. Furthermore, the cross-sectional areas of the individual openings or passageways of the porous material optionally are large or small compared to the length of the individual openings or passageways. The key is that the material presents a restriction to gas flow such that there is pressure drop from the curtain gas inlet side to the region that is in communication with the curtain plate opening and the ion inlet. As some non-limiting examples, the porous material is one of a ceramic material, a porous polymeric material, and a metal mesh or screen or other metal element having a plurality of fine openings defined therethrough. Of course, in the case of a metallic diffuser element, electrically insulating spacers are used in order to prevent the diffuser element from conducting electricity between the voltage bearing curtain plate and the outer electrode. The means for restricting gas flow is preferably cylindrical. For instance, the diffuser has been illustrated as a cylinder that is round in cross-section. Of course, other cross-sectional shapes are also envisaged, such as for instance square or oval. Further optionally, the cross-section is non-uniform across a height of the diffuser. A passageway through the means for restricting gas flow is optionally open or contains a porous material, preferably a porous material that is of higher porosity compared to the rest of the means for restricting gas flow. When the means for restricting gas flow is provided as a metallic element such as a screen or mesh, the openings therethrough are small enough to cause a slight pressure difference between the exterior and the interior of the means for restricting gas flow, as described above. Openings of any suitable shape, such as for instance slots, squares or circles, are optionally provided through the metallic element.

Numerous other embodiments may be envisaged without departing from the spirit and scope of the invention.

What is claimed is:

1. An apparatus for separating ions, comprising:
    a first electrode having a first orifice defined therethrough;
    a FAIMS analyzer comprising a second electrode having a second orifice defined therethrough, the second orifice spaced-apart from and approximately aligned with the first orifice when the apparatus is in an assembled condition;
    a curtain gas chamber defined by a space between the first electrode and the second electrode and being dimensioned larger than a size of either one of the first orifice and the second orifice, the curtain gas chamber including a third orifice for providing a flow of a gas from a gas source into the curtain gas chamber; and,
    a diffuser comprising a porous material and having a length, the diffuser including a passageway extending along the length between a first end of the diffuser and an opposite second end of the diffuser, the passageway being open at the first end and at the second end, the diffuser being disposed within the curtain gas chamber between the third orifice and each of the first and second orifices, and such that both of the first orifice and the second orifice are aligned with the passageway through the diffuser.

2. An apparatus according to claim 1, wherein a cross-sectional area of the passageway taken along a plane perpendicular to the length is dimensioned to be larger than a size of either one of the first orifice and the second orifice.

3. An apparatus according to claim 2, wherein the diffuser substantially blocks a shortest gas flow-path between the third orifice and each of the first and second orifices.

4. An apparatus according to claim 3 wherein the porous material of the diffuser provides a plurality of gas flow-paths through the diffuser.

5. An apparatus according to claim 3, wherein the porous material is a ceramic material.

6. An apparatus according to claim 3, wherein the porous material is a metallic mesh.

7. An apparatus according to claim 3, wherein the porous material is a polymeric material.

8. An apparatus according to claim 4, wherein the diffuser is generally cylindrical and has an outer periphery defining an outer surface and an inner periphery defining the passageway.

9. An apparatus according to claim 8, wherein the porous material has a substantially uniform thickness between the outer periphery and the inner periphery.

10. An apparatus according to claim 9, wherein the thickness of the porous material between the outer periphery and the inner periphery is small relative to a cross-sectional area of the passageway taken along a plane perpendicular to the length.

11. An apparatus for separating ions, comprising:
    a FAIMS analyzer comprising a first electrode and a second electrode disposed in a spaced-apart relationship one relative to the other so as to define an analyzer region therebetween, the first electrode having an inlet orifice defined therethrough for providing fluid communication between the analyzer region and a region that is external to the analyzer region;
    a curtain gas chamber disposed within the region that is external to the analyzer region and in fluid communication with the analyzer region via the inlet orifice, the curtain gas chamber including a curtain gas inlet for receiving a flow of a curtain gas from a curtain gas source, and including a curtain plate electrode having an outlet orifice defined therethrough; and,
    a diffuser disposed within the curtain gas chamber between the first electrode and the curtain plate electrode, the diffuser comprising a porous material having a passageway defined therethrough and open at both ends such that the inlet orifice and the outlet orifice are in fluid communication one with the other via the passageway, and such that the curtain gas inlet is in fluid communication with each of the inlet orifice and the outlet orifice via a plurality of gas flow-paths defined through the porous material.

12. An apparatus according to claim 11, wherein the porous material is a ceramic material.

13. An apparatus according to claim 11, wherein the porous material is a metallic mesh.

14. An apparatus according to claim 11, wherein the porous material is a polymeric material.

15. An apparatus according to claim 11, wherein the diffuser is generally cylindrical and having an outer periphery defining an outer surface and an inner periphery defining the passageway.

16. An apparatus according to claim 15, wherein, the porous material has a substantially uniform thickness between the outer periphery and the inner periphery.

17. An apparatus for separating ions, comprising:
    a FAIMS analyzer comprising a first electrode and a second electrode disposed in a spaced-apart relationship one relative to the other so as to define an analyzer region therebetween, the first electrode having an inlet orifice defined therethrough for providing fluid communication between the analyzer region and a region that is external to the analyzer region;
    a curtain gas chamber disposed adjacent to the inlet orifice, the curtain gas chamber including a curtain gas inlet for receiving a flow of a curtain gas from a curtain gas source and a curtain gas outlet for providing a flow of the curtain gas; and,
    means for restricting gas flow between the curtain gas inlet and the curtain gas outlet such that the flow of curtain gas out of the curtain gas outlet is provided along a direction substantially perpendicular to a plane containing the curtain gas outlet.

18. An apparatus according to claim 17, wherein the means for restricting gas flow comprises a diffuser comprising a porous material.

19. An apparatus according to claim 18, wherein the porous material is a ceramic material.

20. An apparatus according to claim 18, wherein the porous material is a metallic mesh.

21. An apparatus according to claim 18, wherein the porous material is a polymeric material.

22. An apparatus according to claim 17, wherein the means for restricting gas flow forms a substantially gas-tight seal about each one of the curtain gas outlet and the inlet orifice.

23. An apparatus according to claim 22, wherein the means for restricting gas flow includes a passageway extending between opposite ends thereof, the passageway for providing fluid communication between the curtain gas outlet and the inlet orifice.

24. An apparatus according to claim 23, wherein the means for restricting gas flow comprises a porous material disposed between the curtain gas inlet and the passageway, the porous material for supporting a generally symmetrical flow of the curtain gas from the curtain gas chamber inwardly toward the passageway.

25. An apparatus according to claim 17, comprising an ionization source disposed in a spaced-apart arrangement with the curtain gas outlet and in fluid communication therewith for providing a flow of ions along a direction that is generally opposite the flow of curtain gas out of the curtain gas outlet.

26. A method of separating ions, comprising:
providing a FAIMS analyzer region that is in fluid communication with a curtain gas region via a first orifice;
providing an ionization source that is in fluid communication with the curtain gas region via a second orifice;
providing a flow of a curtain gas into the curtain gas region via a third orifice that is spaced-apart from each of the first orifice and the second orifice;
directing the flow of a curtain gas through a porous wall of a diffuser element that is disposed within the curtain gas region and into a passageway within the interior of the diffuser element so as to restrict the flow of a curtain gas between the third orifice and each one of the first orifice and the second orifice;
providing a flow of the curtain gas along the passageway and out through the second orifice along a direction that is substantially perpendicular to a plane containing the second orifice; and,
directing a flow of ions from the ionization source toward the second orifice so as to desolvate the ions in the flow of the curtain gas.

* * * * *